US009295414B1

(12) United States Patent
Chander

(10) Patent No.: US 9,295,414 B1
(45) Date of Patent: Mar. 29, 2016

(54) ADAPTIVE INTERRUPTIONS PERSONALIZED FOR A USER

(71) Applicant: FUJITSU LIMITED, Kawasaki-shi, Kanagawa (JP)

(72) Inventor: Ajay Chander, San Francisco, CA (US)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/495,716

(22) Filed: Sep. 24, 2014

(51) Int. Cl.
*A61B 5/11* (2006.01)
*G08B 21/24* (2006.01)

(52) U.S. Cl.
CPC ................ *A61B 5/1118* (2013.01); *A61B 5/11* (2013.01); *A61B 5/1116* (2013.01); *G08B 21/24* (2013.01)

(58) Field of Classification Search
CPC ....... A61B 5/11; A61B 5/1116; A61B 5/1118
See application file for complete search history.

(56) References Cited

U.S. PATENT DOCUMENTS 7,974,849 B1 * 7/2011 Begole .............. G06Q 10/0631 705/1.1
2006/0004705 A1 1/2006 Horvitz et al.
2006/0041648 A1 2/2006 Horvitz
2010/0131443 A1 * 5/2010 Agarwal .......... G06F 17/30867 706/46
2012/0279285 A1 * 11/2012 Kato ....................... B21D 5/02 73/65.01
2014/0115490 A1 * 4/2014 Yamasani ............ G06F 21/604 715/743
2015/0038806 A1 * 2/2015 Kaleal, III ............ A61B 5/4872 600/301

OTHER PUBLICATIONS

BusyBody: Creating and Fielding Personalized Models of the Cost of Interruption. Horvitz et. al. CSCW, Focused on creating Bayesian models of the cost of interrupting users. Nov. 6, 2004.
Daniel C. McFarlane "The Scope and Importance of Human Interruption in Human—Computer Interaction Design" Human-Computer Interaction, 2002, vol. 17, pp. 1-61.

* cited by examiner

*Primary Examiner* — Van Trieu
(74) *Attorney, Agent, or Firm* — Maschoff Brennan

(57) ABSTRACT

A method of determining an adaptive interruption that is personalized for the user based on conditions of the user includes receiving data describing one or more conditions of a user. The method also includes determining an interruption state for the user based on the one or more conditions of the user and estimating that the user will act based on the interruption state. The method also includes, responsive to estimating that the user will act, determining an adaptive interruption that is personalized for the user based on the one or more conditions of the user.

20 Claims, 6 Drawing Sheets

300

Receive Sensor Data
302

Retrieve Interruption Policy Data
304

Determine Interruption State
306

Retrieve Care Data
308

Determine Adaptive Interruption That Is Personalized For User
310

Instantiate Care
312

Calendar Server 140
Weather Server 145
Social Network Server 150
Second Server 155
Expert 108
Interruption Client 104
Network 107
Client 102
Interruption System 100
User 106
199

Figure 4:
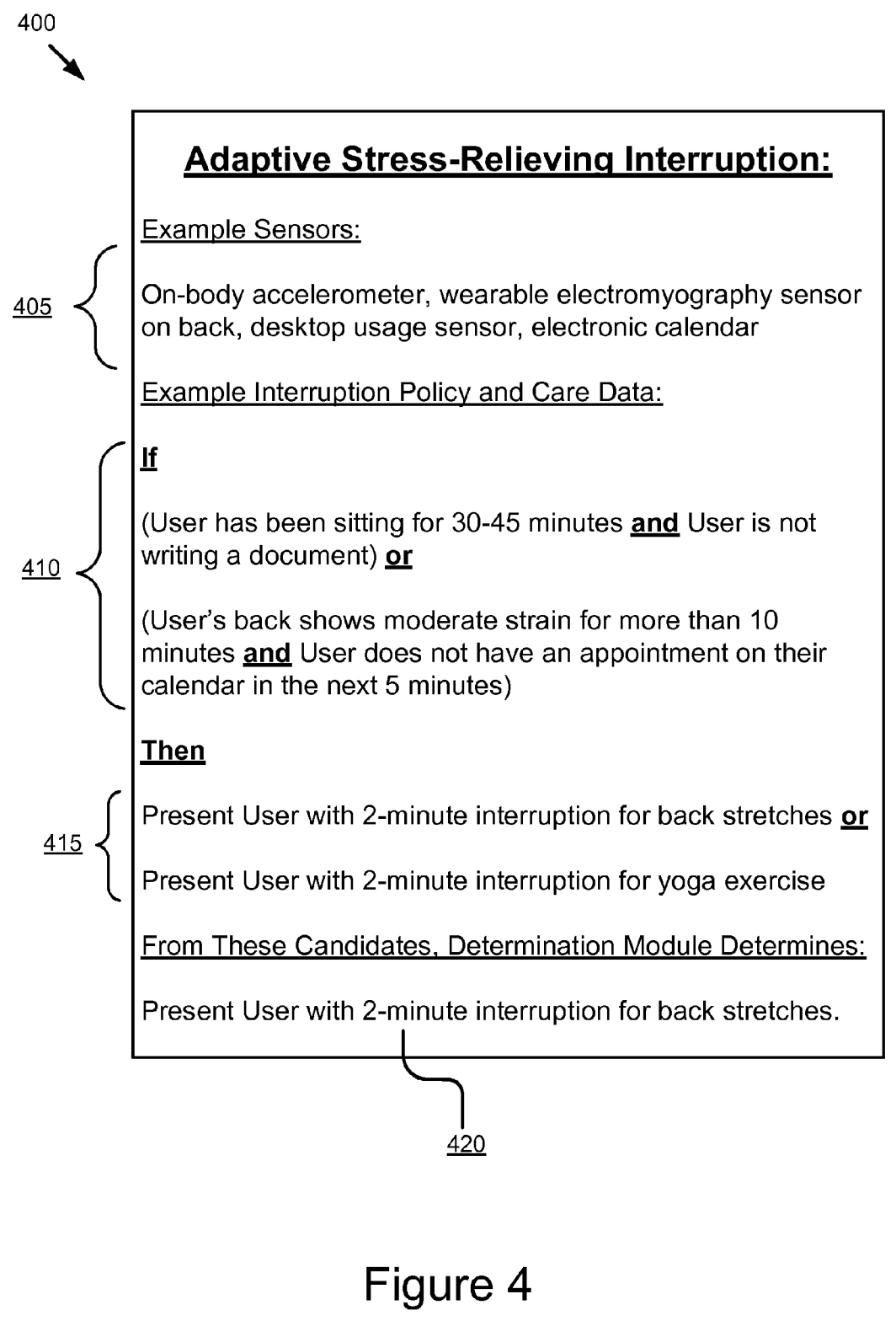

400

Adaptive Stress-Relieving Interruption:

Example Sensors:

405

On-body accelerometer, wearable electromyography sensor on back, desktop usage sensor, electronic calendar Example Interruption Policy and Care Data:

410

If

(User has been sitting for 30-45 minutes and User is not writing a document) or

(User's back shows moderate strain for more than 10 minutes and User does not have an appointment on their calendar in the next 5 minutes)

Then

415

Present User with 2-minute interruption for back stretches or

Present User with 2-minute interruption for yoga exercise

From These Candidates, Determination Module Determines:

Present User with 2-minute interruption for back stretches.

ADAPTIVE INTERRUPTIONS PERSONALIZED FOR A USER

FIELD

The embodiments discussed herein are related to adaptive interruptions personalized for a user.

BACKGROUND

As healthcare costs rise, people are looking for ways to reduce the cost of healthcare. Preventive care may be cheaper than treating injuries and sicknesses. One form of preventive care may be taking breaks to carry out some beneficial activity during the course of the day. During these breaks, a person may rest, exercise, meditate, etc. Such breaks taken to carry out some beneficial activity may be referred to as an “interruption.” Interruptions are beneficial for many different conditions, sicknesses, and injuries, including, for example, repetitive strain injury, diabetes, and hypertension. Timely and personalized interruptions can be instrumental in effecting behavior change. Interruptions have also been shown to increase productivity and decrease absenteeism in the workplace.

SUMMARY

According to an aspect of an embodiment, a method of determining an adaptive interruption that is personalized for the user based on conditions of the user includes receiving data describing one or more conditions of a user. The method also includes determining an interruption state for the user based on the one or more conditions of the user. The method also includes estimating whether the user will act based on the interruption state. The method also includes, responsive to estimating that the user will act, determining an adaptive interruption that is personalized for the user based on the one or more conditions of the user.

The object and advantages of the embodiments will be realized and achieved at least by the elements, features, and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which:

FIG. 4 is a block diagram of an example adaptive interruption configured to relieve stress for a particular user based on conditions of the user.

DESCRIPTION OF EMBODIMENTS

Figure 1A:
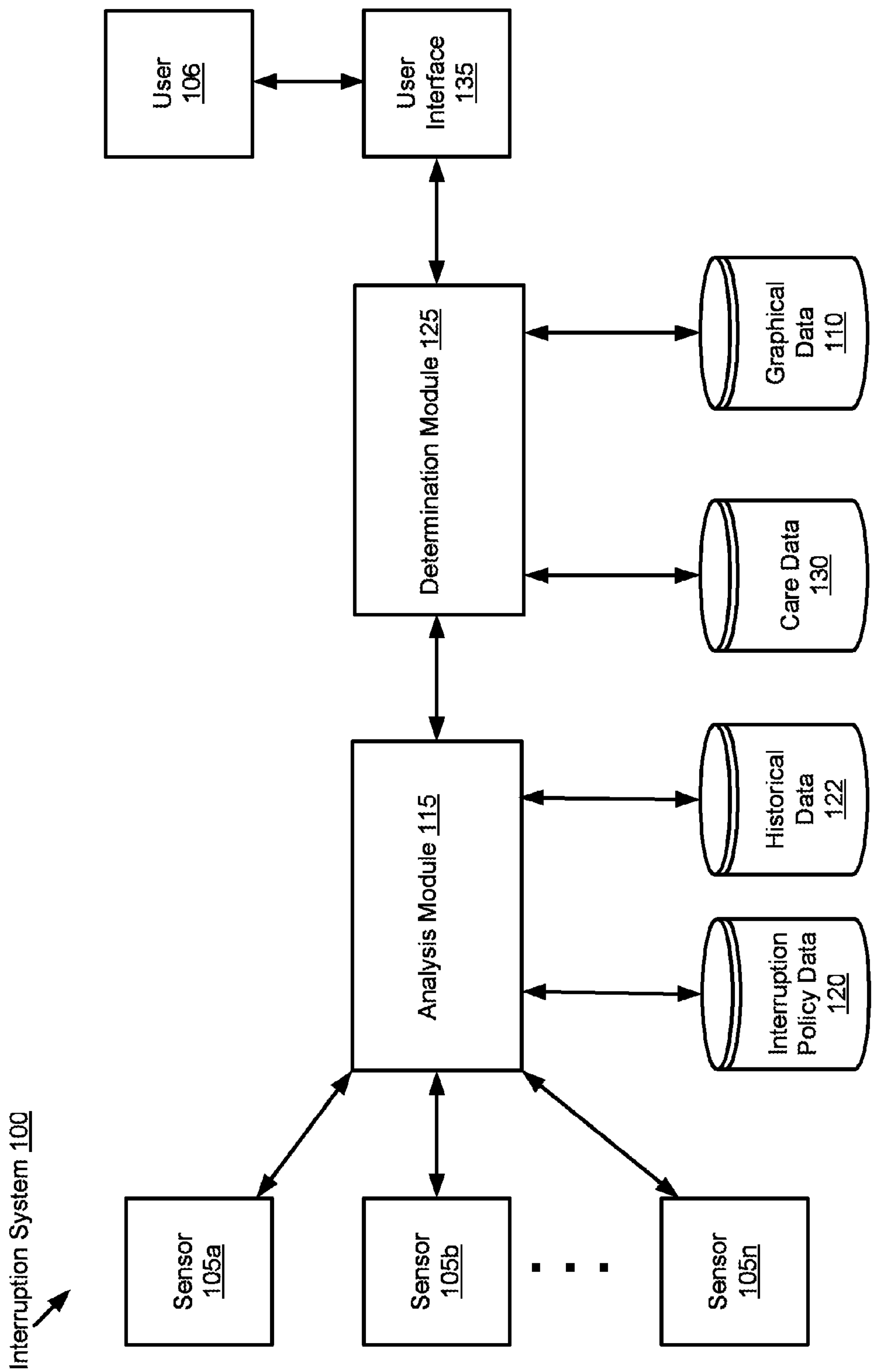
FIG. 1A is a block diagram of an example interruption system.

The embodiments discussed herein are related to providing an adaptive interruption that is personalized for a user based on conditions of the user.

A problem with interruptions may be that people forget to take proactive action to prevent the onset of chronic conditions. For example, if a worker takes an interruption during the workday, the worker may be more likely to produce better quality work product. However, many workers may be too focused on completing their work assignments and, as a result, they may forget to take an interruption.

Applications exist to remind people to take interruptions. However, these existing applications suffer from many deficiencies. For example, these existing applications do not have the ability to be personalized to a user based on the user’s conditions in such a way that the application takes into account the user’s environment state and mental state, the histories of those states, and the history of the user’s receptiveness to such interruptions, prior to providing the user with a reminder to take an interruption. For example, the application may remind a user to take an interruption when the user is in the middle of a meeting. The user may not take the interruption because they are in the middle of the meeting. This is an example of the existing application failing to take into account the user’s environmental state. The application may also provide the user with a reminder to take an interruption when the user has recently arrived at work and does not feel the need to take a break. This is an example of the existing application failing to take into account the user’s mental state. Over time, such reminders which fail to account for the user’s environmental state and mental state may become an annoyance for the user.

Another deficiency in the existing applications may be a reliance on secondary variables such as time. For example, some applications may provide a user with a reminder every 45 minutes (or some other time interval). Such applications are ineffective since they do not take into account the environmental and mental state of the user, the histories of those states, and the history of the user’s receptiveness to such interruptions.

Another deficiency in existing applications may be a reliance on minimizing the costs of interrupting a user who is in the middle of completing a task. For example, these applications may focus on making sure they do not interrupt a user when the user may be busy with a work assignment. This is not the right focus for preventing healthcare-related conditions since it does not take into account the mental state of the user and the user’s willingness to momentarily delay tasks in order to improve their health by taking interruptions. This approach also does not take into account other environmental states such as physical manifestations of the user’s biological state which may be measured using one or more sensors such as a wearable electromyography sensor placed on the user’s back to measure back strain over a prolonged period of time, which is a biological state indicative of the user’s need to take a interruption.

Existing applications may not take into account the user’s biological state in the way described above in the previous paragraph. Taking into account the user’s biological state is beneficial since it enables the application to track the user’s engagement and ability to be interrupted in a manner that complements the user’s need to complete tasks.

Some or all of the foregoing deficiencies may be overcome by the use of adaptive interruptions that are personalized for the user based on conditions of the user. As will be explained in more detail below with reference to FIGS. 1A and 1B, the conditions of the user may be determined and retrieved using various sensors. In some embodiments, the conditions of the user that are used to determine an adaptive interruption that is personalized may include the biological state, the environmental state, the mental state of the user, the histories of those states, and the history of user receptiveness to past interruptions.

An adaptive interruption may be determined by an interruption system. The adaptive interruptions may be configured so that they are presented to the user at the time when the user is most likely to act on the adaptive interruption. The adaptive interruption may be personalized to the user and adaptive to changes in the conditions of the user. Such interruptions may be personalized because they are determined for a particular user based on data that is specific to the user (e.g., sensor data that describes the conditions of the user, historical data that describes the past actions of the user, responsiveness to past adaptive interruptions provided to the user, or a user profile that describes the preferences of the user). The conditions of the user described by the sensor data may include one or more of the biological state of the user, the environmental state of the user, the mental state of the user, the histories of those states, and the history of user receptiveness to past interruptions. Such interruptions may also be adaptive because the conditions of the user may change over time (or the sensors used to determine or retrieve the sensor data describing the conditions of the user may change over time). When such a change occurs, the interruption system may determine a different adaptive interruption for the user. In this way, the adaptive interruptions determined by the interruption system are both personalized to the user and adaptive to changes in the conditions of the user.

Embodiments of the present invention will be explained with reference to the accompanying drawings.

FIG. 1A is a block diagram of an example interruption system 100, arranged in accordance with at least one embodiment described herein. The interruption system 100 may be implemented as a component of a processor-based computing device. For example, the interruption system 100 may be a component of a mobile phone, a smartphone, a tablet computer, a laptop computer, a desktop computer, a set-top box, or a wearable smart device (e.g., a smartwatch, smart glasses, a smart pedometer, or any other wearable smart device).

A user 106 is a human user of the interruption system 100. The interruption system 100 may include a number of sensors 105*a*, 105*b* . . . 105*n* (referred to collectively or individually as "sensor 105" or "sensors 105"). A sensor 105 may determine or retrieve sensor data. The sensor data may include information describing one or more conditions for the user 106. For example, the sensor 105 may be an on-body accelerometer, pedometer, heart rate monitor, wearable electromyography sensor, or desktop usage sensor. The sensor 105 may be a sensor configured to measure one or more of the biological state of the user 106, the environmental state of the user 106, the mental state of the user 106, the histories of those states, and the history of user receptiveness to past interruptions.

In some embodiments, the sensor 105 may also be configured to access electronic data associated with the user 106 or the environment of the user 106. For example, the sensor 105 may be configured to retrieve calendar data describing the user's electronic calendar, social data describing the user's activities on a social network, or weather data describing current and/or forecasted weather for a geographic location in which the user 106 is currently located or may later be located. This embodiment is described in more detail with reference to FIG. 1B.

The calendar data retrieved by the sensor 105 may include a description of the user's appointments, due dates, assignments, etc. For example, the calendar data may be associated with the user's work e-mail account and may describe the user's appointments at work for a specific time or a range of time.

The social data retrieved by the sensor 105 may describe the user's comments, approval indications, posts, or status updates on a social network. For example, the user may access a social network and may make comments indicating that the user is tired and in need of a break. In some embodiments, the social data may be stored in a social graph accessible by the interruption system 100.

The weather data retrieved by the sensor 105 may describe weather conditions associated with a geographic location of the user 106 (hereinafter "the user's geographic location"). For example, the weather data may indicate that the weather associated with the user's geographic location is 80 degrees Fahrenheit and suitable for the user 106 to take a walk outside or engage in some other outdoor activity.

The sensor data may include the calendar data, social data, or weather data. The calendar data, social data, and weather data are described in more detail below with reference to FIG. 1B. In some embodiments, the client 102 is a smartphone and the sensor data is detected by the smartphone sensors, including one or more a light sensor, temperature sensor, etc.

The sensor data may be accessible by the interruption system 100 without the client 102 being communicatively coupled to the network 107. For example, the interruption system 100 may be stored and executed by a mobile processor-based device (e.g., a smartphone, a smart watch, a wearable or connected device, etc.) and using sensor data that is picked up by one or more sensors of the processor-based device itself (e.g., light sensor, temperature sensor, accelerometer, etc. which are an element of the processor-based device).

The sensor data may describe real time or near real time conditions for the user 106. The interruption system 100 may include a memory to store the sensor data. In some embodiments, the interruption system 100 only determines or retrieves sensor data if authorized to do so by the user 106.

The interruption system 100 may include or have access to one or more of interruption policy data 120, historical data 122, care data 130, and/or graphical data 110. The interruption policy data 120, the historical data 122, the care data 130, and the graphical data 110 are described in more detail below.

The interruption policy data 120 may include data describing some of the conditions under which the user 106 may be provided with an adaptive interruption personalized for the user 106. In some embodiments, the interruption policy data 120 may indicate that an adaptive interruption personalized for the user 106 may be based on a combination of two or more conditions of the user 106. The interruption policy data 120 may be stored on a memory accessible by the components of the interruption system 100. Examples of interruption polices are described in more detail below with reference to FIGS. 4 and 5.

The historical data 122 may include data describing the historical conditions under which the user 106 acted on an adaptive interruption provided by the interruption system 100. The historical data 122 may include qualitative data describing how well the user's 106 actions conformed to the adaptive interruption. The historical data 122 may be stored on a memory accessible by the components of the interruption system 100.

An analysis module 115 may include code and routines configured to analyze data to determine whether the interruption system 100 should provide the user 106 with an adaptive interruption. For example, the analysis module 115 may analyze one or more of the sensor data, the historical data 122, and the interruption policy data 120 to determine whether the interruption system 100 should provide the user 106 with an interruption.

In some embodiments, the analysis module 115 may be implemented using hardware including a field-programmable gate array (FPGA) or an application-specific integrated circuit (ASIC). In some other instances, the analysis module 115 may be implemented using a combination of hardware and software. Thus, the analysis module 115 may be implemented as a hardware device.

In some embodiments, the analysis module 115 may receive sensor data from the sensor 105. The sensor data may describe the conditions of the user 106. The analysis module 115 may retrieve the interruption policy data 120. In some embodiments, the analysis module 115 may determine an interruption state for the user 106. The interruption state for the user may indicate whether to provide the user 106 with an adaptive interruption. The interruption state may also indicate whether the user 106 is likely to act on the adaptive interruption. Acting on an interruption may include following the directives of the adaptive interruption. Acting on the adaptive interruption may include the user 106 engaging in a period of action or inaction based on the adaptive interruption provided to the user 106 by the interruption system 100. For example, if the user 106 is provided with an adaptive interruption specifying that the user 106 should take a ten-minute walk outside, then acting on the adaptive interruption may include the user 106 taking a walk outside for ten minutes as specified by the adaptive interruption provided by the interruption system 100. Acting on the adaptive interruption may also be defined as the user carrying out some degree of the recommended action. For example, in this case, we can define that the user acted on the suggestion if they simply walked for any period of time, or if they walked for at least 50% of the suggested time, etc. The extent to which a user acts on a recommended suggestion can also be recorded (and is part of historical data 122).

The analysis module 115 may determine an estimate based on the sensor data or the historical data 122 whether the user 106 is likely to act on the adaptive interruption. The likelihood that the user 106 may act on an adaptive interruption may be expressed as a percentage or any other form that is conducive to expressing the likelihood that an event will occur.

The analysis module 115 may be configured to determine whether a predetermined threshold is satisfied. The analysis module 115 may determine whether the predetermined threshold is satisfied based on the sensor data or the historical data 122. The predetermined threshold may indicate whether the user 106 is likely to act on the interruption.

The interruption system 100 may be configured so that the predetermined threshold is satisfied before the interruption system 100 provides the user 106 with an adaptive interruption. For example, the analysis module 115 may be configured so that if there is at least a 50% likelihood that the user 106 will act on an interruption, the analysis module 115 may determine to provide the user 106 with an adaptive interruption. According to this example embodiment, the analysis module 115 may be configured to determine not to provide the user 106 with an adaptive interruption if the user 106 is not at least 50% likely to act on the interruption.

In some embodiments, the analysis module 115 may be configured to determine the conditions of the user 106 based on one or more of the sensor data, the historical data 122, and the interruption policy data 120. In some embodiments, the conditions of the user 106 are determined based in part on an average of the sensor data over a predetermined period of time.

The analysis module 115 may be configured to transmit one or more of the interruption state, the sensor data, or the historical data 122 to a determination module 125. The determination module 125 may make determinations as described in more detail below based on data received from the analysis module 115 and/or based on the care data 130 and the graphical data 110.

The care data 130 may include data describing different candidate interruptions. The candidate interruptions may describe one or more interruptions that may be selected as an adaptive interruption for the user 106 based on the conditions of the user 106. For example, the candidate interruptions or adaptive interruptions may include one or more of taking a walk outside, walking on an indoor treadmill, meditating, doing yoga, lifting weights, walking inside, stretching, climbing stairs, readjusting workspace furniture, sitting quietly with eyes closed, taking a nap, etc. The care data 130 may be stored on a memory accessible by the components of the interruption system 100.

The graphical data 110 may include data used to generate graphical elements that may be displayed on a user interface 135 of the interruption system 100. For example, the graphical data 110 may include data used to generate a graphical user interface describing an adaptive interruption that is personalized for the user 106 based on the conditions of the user 106.

The determination module 125 may include code and routines configured to determine an adaptive interruption that is personalized for the user 106 based on the conditions of the user 106. The determination may include an adaptive interruption that is personalized for the user 106 based on the conditions of the user 106 as described by one or more of the interruption state, the sensor data, the historical data 122, or the care data 130.

In some embodiments, the determination module 125 may be implemented using hardware including an FPGA or an ASIC. In some other instances, the analysis module 115 may be implemented using a combination of hardware and software.

The adaptive interruption determined by the determination module 125 may be personalized to the user 106 and adaptive to changes in the conditions of the user 106. For example, the determination module 125 may determine the adaptive interruption based on the conditions of the user 106 as described by one or more of the interruption state determined by the analysis module 115, the sensor data, or the historical data 122. Such interruptions may be personalized because they are determined for the particular user 106 based on data that is specific for the user 106 (e.g., sensor data that describes the conditions of the user 106 or the historical data 122 that describes the past actions of the user 106 responsive to past adaptive interruptions provided to the user 106). Such interruptions may also be adaptive because the conditions of the user 106 may change over time (or the sensors used to determine or retrieve the sensor data describing the conditions of the user 106 may change over time). When such a change occurs, the analysis module 115 may determine a different interruption state and the determination module 125 may determine a different adaptive interruption for the user 106. In this way, the adaptive interruptions determined by the determination module 125 are both personalized to the user 106 and adaptive to changes in the conditions of the user 106.

The determination module 125 may retrieve the care data 130 describing a number of different candidate interruptions that may be suitable for the user 106 based on the conditions of the user 106. The determination module 125 may analyze the care data 130 to determine an adaptive interruption personalized for the user 106 based on the user's conditions as described by one or more of the interruption state, the sensor data, or the historical data 122.

In some embodiments, the determination module 125 may use the historical data 122 to determine an adaptive interruption personalized for the user 106 that is more likely to be acted on by the user 106.

In some embodiments, different candidate interruptions described by the care data 130 may correspond to different user conditions or interruption states. For example, assume that the sensor data indicates that the user 106 is stressed and that the weather outside is conducive to talking a walk outside. The determination module 125 may determine that these user conditions indicate an adaptive interruption that includes a walk outside. By contrast, if the sensor data indicates that the user 106 is stressed but the weather outside is not conducive to taking a walk outside, then the determination module 125 may determine that these user conditions indicate an adaptive interruption that includes a walk inside on a treadmill since, for example, an adaptive interruption that includes a walk outside under these particular weather conditions may be unlikely to be acted on by the user 106. The determination module 125 may be configured to analyze the care data 130, the sensor data describing the user's conditions, the historical data 122, or the interruption state to determine an adaptive interruption from the candidate interruptions described by the care data 130. The adaptive interruption may correspond to the conditions of the user 106.

The determination module 125 may be configured to determine the graphical data 110. For example, the determination module 125 may determine the graphical data 110 describing an adaptive interruption that is personalized for the user 106 based on the conditions of the user 106. The determination module 125 may transmit the graphical data to the user interface 135 for display on the user interface 135. Alternatively, the interruption system 100 may be configured to provide the adaptive interruption to the user verbally or using an audio signal that indicates a particular interruption.

The user interface 135 may include a display, monitor, or screen used to display graphical data describing an adaptive interruption that is personalized for the user 106 based on the conditions of the user 106. For example, the user interface 135 may include a computer monitor that is communicatively coupled to a desktop computer or set-top box that stores and executes some or all of the components of the interruption system 100. In some embodiments, the user interface 135 may include a screen of a mobile phone, a smartphone, a tablet computer, a laptop computer, or a wearable smart device (e.g., a smartwatch, smart glasses, a smart pedometer, or any other wearable smart device). In some embodiments, the user interface 135 may be a speaker or some other hardware used to reproduce an audio signal.

Figure 1B:
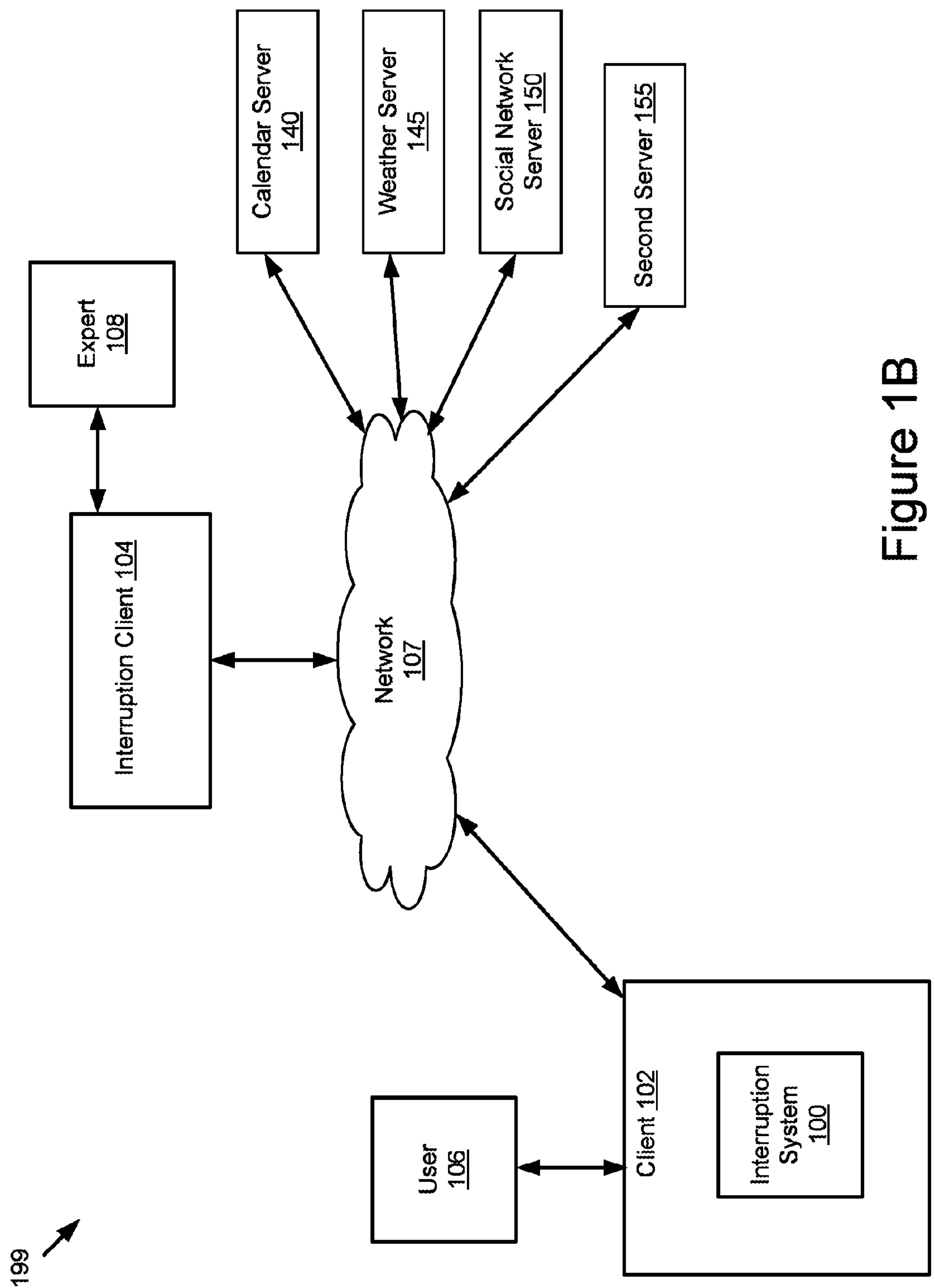
FIG. 1B is a block diagram of an example operating environment in which an interruption system may be implemented.

FIG. 1B is a block diagram of an example operating environment 199 including the interruption system 100. The illustrated operating environment 199 includes a client 102, the interruption system 100, the user 106, a network 107, an interruption client 104, an expert 108, a calendar server 140, a weather server 145, a social network server 150, and a second server 155.

Although FIG. 1B illustrates one network 107 coupled to the client 102, the interruption client 104, the calendar server 140, the weather server 145, the social network server 150, and the second server 155, in practice one or more networks 105 may be connected to these entities.

The network 107 may be a conventional type, wired, or wireless, and may have numerous different configurations including a star configuration, token ring configuration, or other configurations. Furthermore, the network 107 may include a local area network (LAN), a wide area network (WAN) (e.g., the Internet), and/or other interconnected data paths across which multiple devices may communicate. In some instances, the network 107 may be a peer-to-peer network. The network 107 may also be coupled to or include portions of a telecommunications network for sending data in a variety of different communication protocols. In some instances, the network 107 includes Bluetooth communication networks or a cellular communication network for sending and receiving data including via short messaging service (SMS), multimedia messaging service (MMS), hypertext transfer protocol (HTTP), direct data connection, wireless application protocol (WAP), e-mail, etc.

The client 102 may be a processor-based computing device. In some embodiments, the client 102 may be any hardware device that includes a processor, a memory, and network communication capabilities. For example, the client 102 may be a mobile phone, a smartphone, a tablet computer, a laptop computer, a desktop computer, a set-top box, or a wearable smart device (e.g., a smartwatch, smart glasses, a smart pedometer, or any other wearable smart device).

The client 102 may include the interruption system 100. The interruption system 100 was described above with reference to FIG. 1A, and that description will not be repeated here. The user 106 may be a human user of the client 102 or the interruption system 100. The client 102 or the interruption system 100 may include one or more sensors, e.g., sensors 105, that provide sensor data describing the conditions of the user 106. For example, the client 102 or the interruption system 100 may include a desktop usage sensor, an accelerometer, a pedometer, a heart rate monitor, or any other sensor.

The social network server 150 may be a hardware server that includes a processor, a memory, and network communication capabilities. In some implementations, the social network server 150 may send data to the client 102, the interruption client 104, the calendar server 140, the weather server 145, and/or the second server 155 via the network 107. The social network server 150 may also receive data from the client 102, the interruption client 104, the calendar server 140, the weather server 145, and/or the second server 155 via the network 107.

The social network server 150 may include a social network application configured to provide a social network service to one or more users 106. A social network may be a type of social structure where the users 106 may be connected by a common feature. The common feature may include relationships/connections, e.g., friendship, family, work, an interest, etc. The common features may be provided by one or more social networking systems including explicitly defined relationships and relationships implied by social connections with other online users, where the relationships form a social graph. In some examples, the social graph may reflect a mapping of these users 106 and how they may be related. Furthermore, the social network server 150 may be representative of one social network and that there may be multiple social networks coupled to the network 107, each having its own server and social graph. For example, a first social network may be more directed to business networking, a second may be more directed to or centered on academics, a third may be more directed to local business, a fourth may be directed to dating, and others may be of general interest or a specific focus.

The social network server 150 may provide sensor data to the interruption system 100 via the network 107. The user 106 may publish information to the social network associated with a condition of the user 106. For example, the user 106 may publish a status update to the social network indicating that the user 106 is tired or needs a break. The user 106 may have authorized the social network server 150 to provide this information to the interruption system 100. The interruption system 100 may request sensor data associated with the user 106 from the social network server 150 via the network 107. The social network server 150 may transmit the sensor data to the interruption system 100 via the network 107. The sensor data provided to the interruption system 100 may include the information published by the user 106 to the social network.

The calendar server 140 may be a hardware server that includes a processor, a memory, and network communication capabilities. The calendar server 140 may store and execute code and routines configured to provide a calendar service to the client 102. The calendar service may be a cloud-based calendar service or any other form of calendar service. For example, the calendar service may be Google™ Calendar, Microsoft Exchange Server™, or any other calendar service. The calendar server 140 sends and receives data to and from other entities of the operating environment 199 via the network 107. While FIG. 1B includes one calendar server 140, the operating environment 199 may include one or more calendar servers 140.

The calendar server 140 may provide sensor data to the interruption system 100 via the network 107. The user 106 may have a calendar which may include sensor data describing the user's appointments, due dates, assignments, etc. For example, the calendar data may be associated with a work e-mail account of the user 106 and describe the user's 106 appointments at work for a specific time or a range of time. The calendar may also be associated with a personal e-mail account of the user 106. The user 106 may have authorized the calendar server 140 to provide the sensor data to the interruption system 100. The interruption system 100 may request the sensor data associated with the user 106 from the calendar server 140 via the network 107. The calendar server 140 may transmit the sensor data to the interruption system 100 via the network 107.

The weather server 145 may be a hardware server that includes a processor, a memory, and network communication capabilities. The weather server 145 may store and execute code and routines configured to provide a weather service. The weather service may provide sensor data to the client 102 describing the weather conditions associated with the user 106. For example, the weather service may include AccuWeather™, Intellicast™, the National Weather Service, or any other network-accessible weather service. The weather server 145 sends and receives data to and from other entities of the operating environment 199 via the network 107. While FIG. 1B includes one weather server 145, the operating environment 199 may include one or more weather servers 145.

The weather server 145 may provide sensor data to the interruption system 100 via the network 107. For example, the weather server 145 may provide sensor data describing the weather conditions for a geographic location of the user 106. The sensor data may also include a description of the outdoor activities that may be suitable for the user's geographic location based on the weather conditions associated with the user's geographic location. The interruption system 100 may request sensor data associated with the user 106 from the weather server 145 via the network 107. The weather server 145 may transmit the sensor data to the interruption system 100 via the network 107.

The second server 155 may be a hardware server that includes a processor, a memory, and network communication capabilities. The second server 155 may store and execute code and routines configured to provide the interruption system 100 with sensor data describing the conditions for the user 106. The second server 155 sends and receives data to and from other entities of the operating environment 199 via the network 107. While FIG. 1 includes one second server 155, the operating environment 199 may include one or more second servers 155.

The second server 155 may provide sensor data to the interruption system 100 via the network 107. The interruption system 100 may request sensor data associated with the user 106 from the second server 155 via the network 107. The second server 155 may transmit the sensor data to the interruption system 100 via the network 107.

The expert 108 may be a human that has expertise in determining an adaptive interruption for the user 106.

The interruption client 104 may be a processor-based computing device. In some embodiments, the interruption client 104 may be any hardware device that includes a processor, a memory, and network communication capabilities. For example, the interruption client 104 may be a mobile phone, a smartphone, a tablet computer, a laptop computer, a desktop computer, a set-top box, or a wearable smart device (e.g., a smartwatch, smart glasses, a smart pedometer, or any other wearable smart device).

The interruption client 104 may receive data from the client 102 or the interruption system 100 via the network 107. For example, the interruption client 104 may receive one or more of the following from the client 102 or the interruption system 100: sensor data from the client 102 describing one or more conditions for the user 106; the historical data 122 describing the historical conditions under which the user 106 acted on an adaptive interruption provided by the interruption system 100 or the quality of the user's 106 past action; data describing an interruption state determined by the analysis module 115 of the interruption system 100; or data describing an adaptive interruption that is determined by the determination module 125 of the interruption system 100. The expert 108 may approve the adaptive interruption determined by the determination module 125. The interruption client 104 may transmit data to the client 102 or the interruption system 100 describing the approval of the expert 108. In some embodiments, the expert 108 may review the data received from the client 102 or the interruption system 100 and determine a new adaptive interruption for the user 106 based on the data and the expertise of the expert 108. The interruption client 104 may transmit data to the client 102 or the interruption system 100 describing the new adaptive interruption personalized for the user 106 based on the conditions of the user 106.

Figure 2:
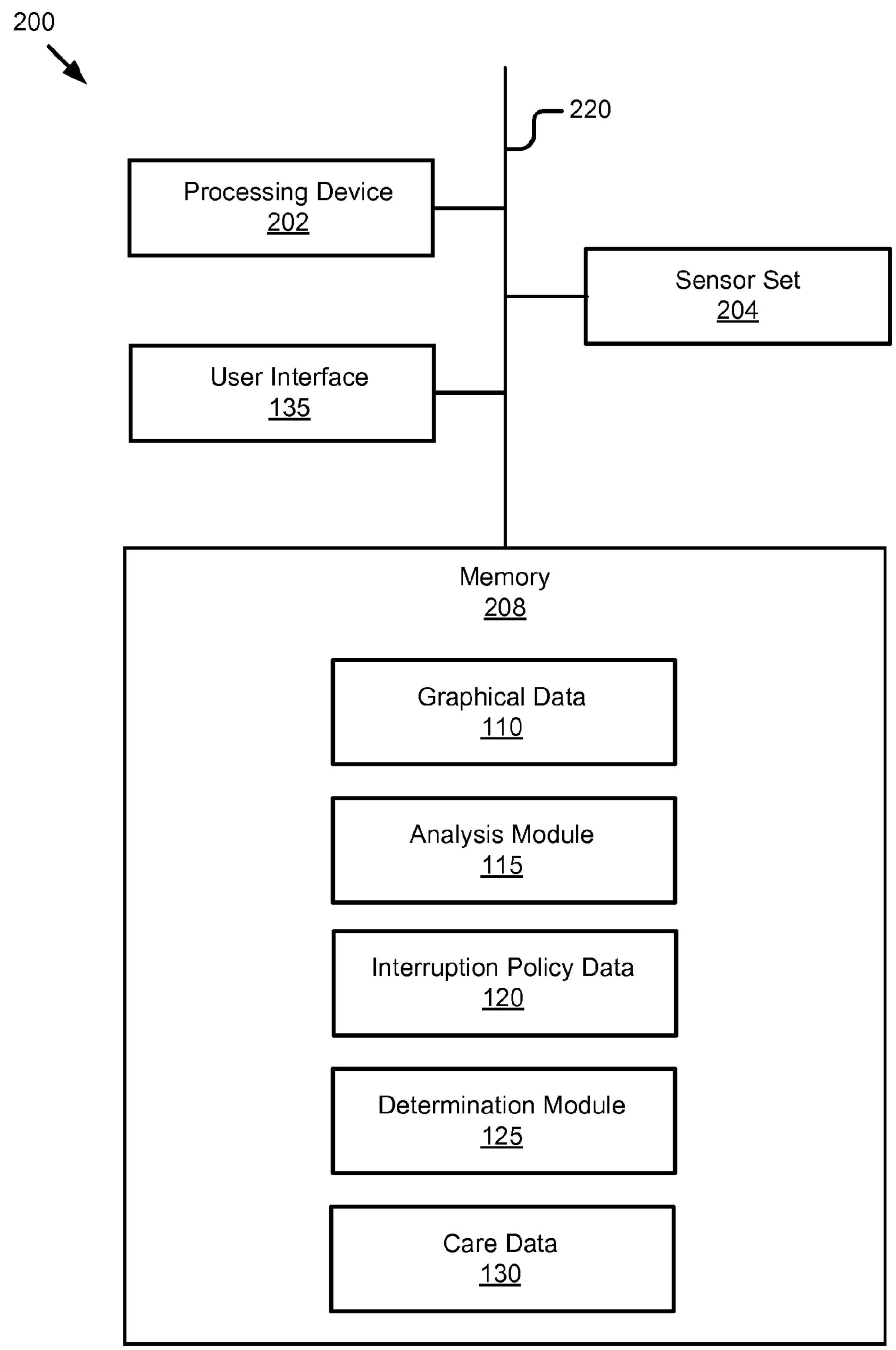
FIG. 2 is a block diagram of an example system for providing an adaptive interruption personalized for a user based on conditions of the user.

FIG. 2 is a block diagram of an example system 200 of determining an adaptive interruption that is personalized for the user 106 based on the conditions of the user 106, arranged in accordance with at least one embodiment described herein. The system 200 of FIG. 2 is an example embodiment of the interruption system 100 of FIGS. 1A and 1B. In some embodiments, the system 200 may be a mobile phone, a smartphone, a tablet computer, a laptop computer, a desktop computer, a set-top box, or a wearable smart device (e.g., a smartwatch, smart glasses, a smart pedometer, or any other wearable smart device).

The system 200 may include a processing device 202, a sensor set 204, the user interface 135, and a memory 208. The various components of the system 200 may be communicatively coupled to one another via a bus 220.

The processing device 202 may be an arithmetic logic unit, a microprocessor, a general purpose controller, or some other processor array to perform computations and provide electronic display signals to a display device. The processing device 202 processes data signals and may include various computing architectures including a complex instruction set computer (CISC) architecture, a reduced instruction set computer (RISC) architecture, or an architecture implementing a combination of instruction sets. Although FIG. 2 includes the single processing device 202, multiple processing devices 202 may be included. Other processors, operating systems, sensors, displays, and physical configurations are possible.

The sensor set 204 includes one or more of the sensors 105 described above with reference to FIGS. 1A and 1B. The sensors 105 were described above with reference to FIGS. 1A and 1B, and that description will not be repeated here. The user interface 135 was also described with reference to FIGS. 1A and 1B, and that description will also not be repeated here.

The memory 208 may store instructions and/or data that may be executed by the processing device 202. The instructions and/or data may include code for performing the techniques described herein. In some embodiments, the instructions may include instructions and data which cause the processing device 202 to perform a certain function or group of functions.

In some embodiments the memory 208 may include a computer-readable media for carrying or having computer-executable instructions or data structures stored thereon. Such computer-readable media may be any available media that may be accessed by a processing device 202 that is programmed to execute the computer-executable instructions stored on the computer-readable media. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other non-transitory storage medium which may be used to carry or store desired program code in the form of computer-executable instructions or data structures and which may be accessed by the processing device 202. Combinations of the above may also be included within the scope of computer-readable media.

In the depicted embodiment, the memory 208 may store the graphical data 110, the analysis module 115, the interruption policy data 120, the determination module 125, and the care data 130. These components of the system 200 were described above with reference to FIGS. 1A and 1B, and their descriptions will not be repeated here. As used herein, the terms "module" or "component" may refer to specific hardware implementations configured to perform the operations of the module or component and/or software objects or software routines that may be stored on and/or executed by the system 200. In some embodiments, the different components and modules described herein may be implemented as objects or processes that execute on a computing system (e.g., as separate threads). While some of the system and methods described herein are generally described as being implemented in software (stored on and/or executed by the system 200), specific hardware implementations or a combination of software and specific hardware implementations are also possible and contemplated. In this description, a "computing entity" may be any computing system as previously defined herein, or any module or combination of modules running on a computing system such as the system 200.

Figure 3:
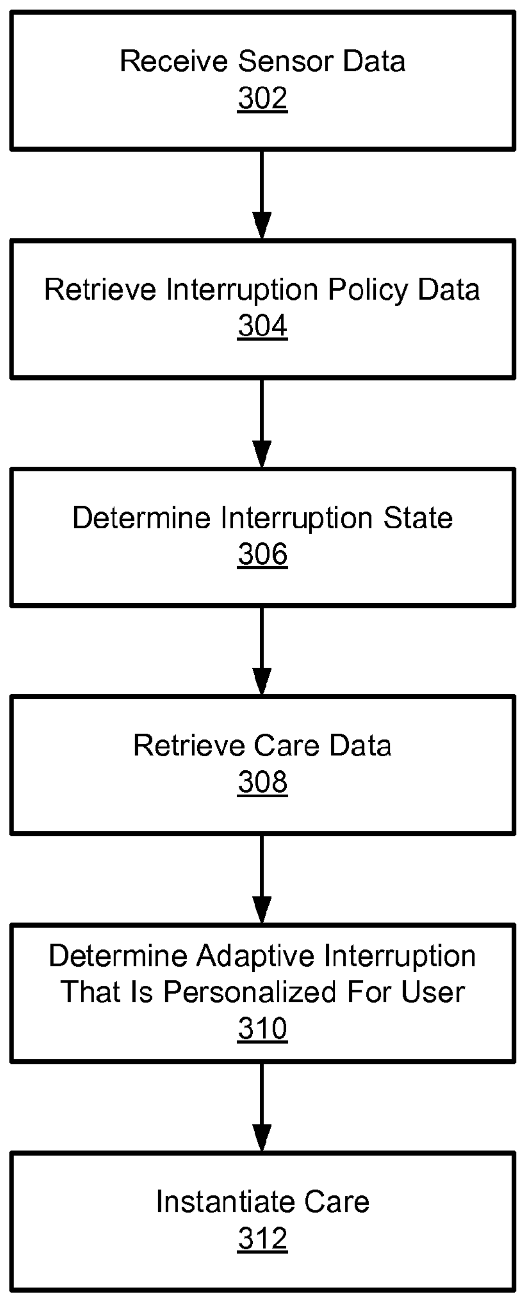
FIG. 3 shows an example flow diagram of a method of operating an interruption system.

FIG. 3 shows an example flow diagram of a method 300 of determining an adaptive interruption that is personalized for the user 106 based on the conditions of the user 106, arranged in accordance with at least one embodiment described herein. The method 300 in some embodiments is performed by a system such as the interruption system 100 of FIGS. 1A and 1B or the system 200 of FIG. 2. For instance, the processing device 202 of FIG. 2 may be configured to execute computer instructions stored on the memory 208 to perform functions and operations as represented by one or more of the blocks of the method 300 of FIG. 3. Although illustrated as discrete blocks, various blocks may be divided into additional blocks, combined into fewer blocks, or eliminated, depending on the desired implementation. The method 300 is described below with reference to FIGS. 1A, 1B, and 2.

The method 300 may begin at block 302. At block 302, sensor data may be received. For example, the analysis module 115 may receive sensor data from the sensor 105. The method 300 may include storing the sensor data in a memory such as the memory 208. For example, the analysis module 115 may store the sensor data in the memory 208.

In some embodiments, the method 300 may include retrieving the historical data 122 describing the historical conditions under which a user acted on an adaptive interruption that is personalized for the user 106. For example, the analysis module 115 may retrieve the historical data 122 from a memory such as the memory 208.

At block 304, the interruption policy data 120 may be retrieved. For example, the analysis module 115 may retrieve the interruption policy data 120 from a memory such as the memory 208. Although not illustrated in FIG. 3, the method 300 may include determining the conditions of the user 106 based on one or more of the sensor data, the historical data 122, and the interruption policy data 120. In some embodiments, the conditions of the user 106 are determined based in part on an average of the sensor data over a predetermined period of time.

At block 306, an interruption state may be determined. For example, the analysis module 115 may determine the interruption state. In some embodiments, the analysis module 115 may determine the interruption state based on one or more of the sensor data, the historical data 122, and the interruption policy data 120. In some embodiments, the interruption state is determined based in part on the conditions of the user 106 determined by the analysis module 115.

In some embodiments, the method 300 may include transmitting one or more of the sensor data, the historical data 122, the interruption policy data 120, and data describing the interruption state determined by the analysis module 115. For example, the analysis module 115 may transmit one or more of the following data to the determination module 125: sensor data; the historical data 122; the interruption policy data 120; and data describing the interruption state determined by the analysis module 115.

At block 308, the care data 130 may be retrieved. For example, the determination module 125 may retrieve the care data 130 from a memory such as the memory 208.

At block 310, an adaptive interruption that is personalized for the user 106 may be determined. For example, the determination module 125 may determine the adaptive interruption that is personalized for the user 106 based on the conditions of the user 106.

In some embodiments, the method 300 may include the determination module 125 transmitting data describing the adaptive interruption, the care data 130, the sensor data, the historical data 122, and the interruption state determined by the analysis module 115 to the interruption client 104 via the network 107. The interruption client 104 may be accessible by the expert 108 who may review one or more of the adaptive interruption, the care data, the sensor data, and the interruption state. The expert 108 may approve the adaptive interruption or suggest an alternative adaptive interruption for the user 106.

At block 312, the determination module 125 may instantiate care. For example, the determination module 125 may access a memory such as the memory 208 and may determine graphical data for displaying a graphical user interface that describes the adaptive interruption determined in block 310 of the method 300. The determination module 125 may transmit the graphical data to the user interface 135. The user interface 135 may generate graphical elements describing the adaptive interruption for display to the user 106.

Some embodiments described herein include a non-transitory computer-readable medium having computer instructions stored thereon that are executable by a processing device to perform one or more of the operations included in the method 300 of FIG. 3, such as the operations illustrated by blocks 302, 304, 306, 308, 310, or 312 in FIG. 3, or variations thereof. The non-transitory computer-readable medium may include the memory 208 of FIG. 2, for example. The processing device may include the processing device 202 of FIG. 2, for example.

FIG. 4 is a block diagram of an example adaptive interruption 400 configured to relieve stress for the particular user 106 based on the conditions of the user 106.

Element 405 includes one or more sensors 105 that may be used to determine or retrieve sensor data that is relevant to this adaptive interruption 400. The sensors 105 included in element 405 may be one or more of the following: an on-body accelerometer; a wearable electromyography sensor that may be applied to the user's 106 back; a desktop usage sensor that may be communicatively coupled to the client 102 accessible by the user 106; and an electronic calendar that may be accessible by the client 102.

Element 410 includes example interruption policy data 120. The interruption policy data 120 included in element 410 may specify that the user 106 may need an adaptive interruption if one of the following conditions of the user 106 is indicated by the sensor data: (1) the user 106 has been sitting for 30 to 45 minutes and the user 106 is not writing a document; or (2) the back of the user 106 shows moderate strain for more than ten minutes and the user 106 does not have an appointment on their calendar in the next five minutes.

Element 415 includes some candidate interruptions based on the conditions of the user 106. The candidate interruptions may be an example of care data 130. The candidate interruptions include: (1) present the user 106 with a two-minute interruption for back stretches; and (2) present the user 106 with a two-minute interruption for yoga exercises. In some embodiments, the determination module 125 may be configured to order the candidate interruptions in a ranked list.

Element 420 includes the adaptive interruption determined for the user 106 by the determination module 125 based on the conditions of the user 106. Here, the determination module 125 has determined to present the user 106 with a two-minute interruption for back stretches. The determination module 125 may have selected this adaptive interruption from the candidate interruptions if, for example, the historical data 122 for the user 106 indicates that the user 106 is not likely to act on an interruption that includes yoga. In some embodiments, the historical data 122 may include user profile data indicating that the user 106 does not enjoy yoga, and so the determination module 125 may select the other candidate interruption which does not include yoga.

Figure 5:
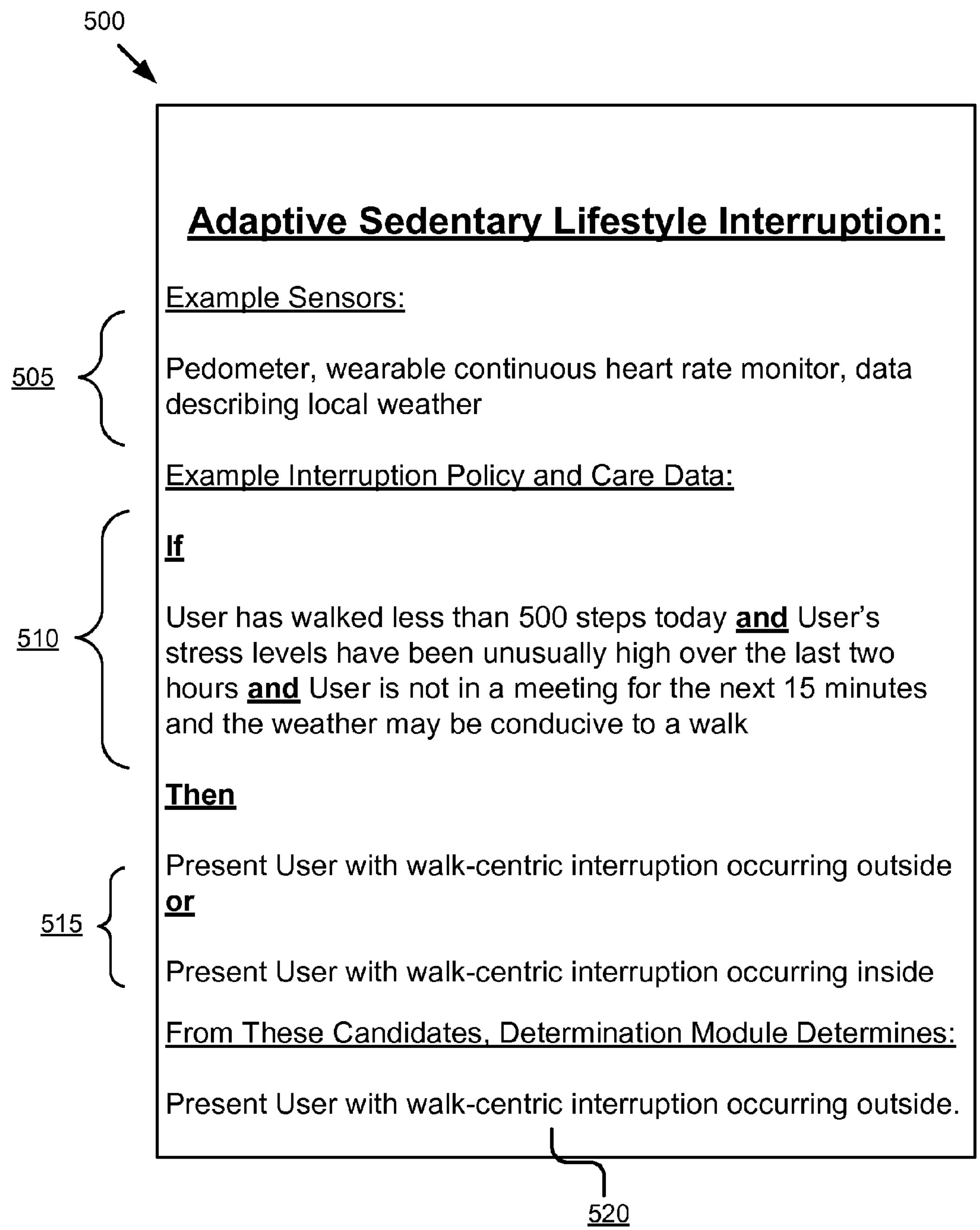
FIG. 5 is a block diagram of an example adaptive interruption configured to mitigate a sedentary lifestyle of a particular user based on conditions of the user.

FIG. 5 is a block diagram of an example adaptive interruption configured to mitigate a sedentary lifestyle of the particular user 106 based on the conditions of the user 106.

Element 505 includes one or more sensors 105 that may be used to determine or retrieve sensor data that is relevant to this adaptive interruption 500. The sensors 105 included in element 505 may be one or more of the following: a pedometer; a wearable continuous heart rate monitor; and data describing the weather for the geographic location of the user 106.

Element 510 includes example interruption policy data 120. The interruption policy data 120 included in element 510 may specify that the user 106 may need an adaptive interruption if one of the following conditions of the user 106 is indicated by the sensor data: (1) the user 106 has walked less than 500 steps today; and (2) the user's 106 stress levels have been unusually high over the past two hours.

Element 515 includes some candidate interruptions based on the conditions of the user 106. The candidate interruptions may be examples of care data 130. The candidate interruptions include: (1) present the user 106 with a walk-centric interruption occurring outside; and (2) present the user 106 with a walk-centric interruption occurring inside.

Element 520 includes the adaptive interruption determined for the user 106 by the determination module 125 based on the conditions of the user 106. Here, the determination module 125 has determined to present the user 106 with a walk-centric interruption occurring outside. The determination module 125 may have selected this adaptive interruption from the candidate interruptions since, for example, the sensor data indicated that the weather outside is conducive to walking.

The embodiments described herein may include the use of a special purpose or general purpose computer including various computer hardware or software modules, as discussed in greater detail below.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A method comprising:

receiving data describing one or more conditions of a user;

determining an interruption state for the user based on the one or more conditions of the user;

estimating that the user will act based on the interruption state; and responsive to estimating that the user will act, determining an adaptive interruption that is personalized for the user based on the one or more conditions of the user.

2. The method of claim 1, wherein the data comprises sensor data describing the one or more conditions of the user.

3. The method of claim 2, wherein the sensor data includes data retrieved via a network and the sensor data includes one or more of the following:

social network data describing interactions of the user with a social network;

weather data describing current or forecasted weather for a geographic location of the user; and calendar data describing an electronic calendar of the user for a specific period of time.

4. The method of claim 1, wherein the data comprises historical data describing one or more historical conditions under which the user acted on one or more historical adaptive interruptions.

5. The method of claim 4, wherein the adaptive interruption is configured to increase a likelihood that the user will act on the adaptive interruption based in part on the historical data.

6. The method of claim 1, wherein the adaptive interruption is determined from a set of candidate interruptions that correspond to the one or more conditions of the user.

7. The method of claim 1, wherein estimating that the user will act based on the interruption state includes determining whether a predetermined threshold is satisfied.

8. A non-transitory computer-readable medium having computer instructions stored thereon that are executable by a processing device to perform operations comprising:

receiving data describing one or more conditions of a user;

determining an interruption state for the user based on the one or more conditions of the user;

estimating that the user will act based on the interruption state; and responsive to estimating that the user will act, determining an adaptive interruption that is personalized for the user based on the one or more conditions of the user.

9. The non-transitory computer-readable medium of claim 8, wherein the data comprises sensor data describing the one or more conditions of the user.

10. The non-transitory computer-readable medium of claim 9, wherein the sensor data includes data retrieved via a network and the sensor data includes one or more of the following:

social network data describing interactions of the user with a social network;

weather data describing current or forecasted weather for a geographic location of the user; and calendar data describing an electronic calendar of the user for a specific period of time.

11. The non-transitory computer-readable medium of claim 9, wherein the sensor data includes data received from one or more sensors including one or more of an on-body accelerometer, a pedometer, a heart rate monitor, a wearable electromyography sensor and a desktop usage sensor.

12. The non-transitory computer-readable medium of claim 9, wherein the one or more conditions of the user include one or more of a biological state of the user, an environmental state of the user and a mental state of the user.

13. The non-transitory computer-readable medium of claim 8, wherein the data comprises historical data describing one or more historical conditions under which the user acted on one or more historical adaptive interruptions.

14. The non-transitory computer-readable medium of claim 13, wherein the adaptive interruption is configured to increase a likelihood that the user will act on the adaptive interruption based in part on the historical data.

15. The non-transitory computer-readable medium of claim 8, wherein the adaptive interruption is determined from a set of candidate interruptions that correspond to the one or more conditions of the user.

16. The non-transitory computer-readable medium of claim 15, wherein the adaptive interruptions are determined based on care data describing the set of candidate interruptions.

17. The non-transitory computer-readable medium of claim 8, wherein the adaptive interruption includes an active activity.

18. The non-transitory computer-readable medium of claim 17, wherein the active activity includes one or more of an outside walk, an inside walk, a yoga session, a weight lifting session and a stretching session.

19. The non-transitory computer-readable medium of claim 8, wherein the adaptive interruption includes a passive activity.

20. The non-transitory computer-readable medium of claim 19, wherein the passive activity includes one of more of a meditation session, a nap and a session of sitting with eyes closed.

* * * * *